US006999854B2

(12) United States Patent
Roth

(10) Patent No.: US 6,999,854 B2
(45) Date of Patent: Feb. 14, 2006

(54) MEDICAL INFUSION PUMP CAPABLE OF LEARNING BOLUS TIME PATTERNS AND PROVIDING BOLUS ALERTS

(75) Inventor: Steven W. Roth, Oronoco, MN (US)

(73) Assignee: International Business Machines Corporation, Armonk, NY (US)

( * ) Notice: Subject to any disclaimer, the term of this patent is extended or adjusted under 35 U.S.C. 154(b) by 111 days.

(21) Appl. No.: 10/857,709

(22) Filed: May 28, 2004

(65) Prior Publication Data

US 2005/0278073 A1    Dec. 15, 2005

(51) Int. Cl.
G05D 11/00    (2006.01)
G05D 7/00    (2006.01)
A61M 31/00    (2006.01)

(52) U.S. Cl. ........................................ 700/282; 604/65
(58) Field of Classification Search ................ 700/282; 604/65

See application file for complete search history.

(56) References Cited

U.S. PATENT DOCUMENTS

| | | | | |
|---|---|---|---|---|
| 4,469,481 | A | | 9/1984 | Kobayashi .................. 604/67 |
| 4,776,842 | A | | 10/1988 | Franetzki et al. ............. 604/67 |
| 5,795,327 | A | * | 8/1998 | Wilson et al. ................ 604/65 |
| 6,198,383 | B1 | | 3/2001 | Sekura et al. ............ 340/309.4 |
| 6,650,951 | B1 | | 11/2003 | Jones et al. .................... 700/90 |
| 2003/0114836 | A1 | | 6/2003 | Estes et al. .............. 604/890.1 |
| 2003/0160683 | A1 | | 8/2003 | Blomquist ............. 340/309.16 |
| 2003/0176933 | A1 | | 9/2003 | Lebel et al. .................. 700/90 |
| 2003/0195462 | A1 | | 10/2003 | Mann et al. ................... 604/67 |
| 2004/0044272 | A1 | | 3/2004 | Moerman et al. ........... 600/300 |
| 2004/0073329 | A1 | | 4/2004 | Engleson et al. ........... 700/131 |

OTHER PUBLICATIONS http://216.239.41.104/search?q=cache:-ZHPMXYdD5MJ: www.logimedix.com/pr20020815.htm+cozmo. . . Deltec Inc. Received 510k Clearance for Insulin Pump, Aug. 15, 2002.
http://216.239.41.104/search?q=cache:MxHBVd9__-RoJ: www.childrenwithdiabetes.com/chat/transcript/d. . . Deltec Cozmo Chat, Nov. 12, 2002.
"Insulin Pumps", Diabetes Forecast, Jan. 2004, RG28-RG29.
http://216.239.41.104/search?q=cache:AIrrVZX13YkJ: www.delteccozmo.com/specs.cfm+bolus+alarm+. . . Deltec Cozmo® Insulin Pump Specifications.
http://216.239.41.104/search?q=cache:YFVGkJOaUpEJ: www.delteccozmo.com/stories__02.cfm+cozmo+. . . , Deltec Cozmo® Insulin Pump User Stories.

* cited by examiner

Primary Examiner—Leo Picard
Assistant Examiner—Ryan Jarrett
(74) Attorney, Agent, or Firm—Robert R. Williams

(57) ABSTRACT

An apparatus and method are disclosed for improving a medical infusion pump. Users of medical infusion pumps, such as insulin pumps, require a bolus of a medication at predicable times of the day, such as at or near mealtimes for insulin pumps. The disclosed medical infusion pump determines bolus time intervals during which boluses are usually taken, and, alerts the user at one or more calculated alert times during an active bolus time interval when a bolus has not yet been delivered during the active bolus time interval. Advantageously, a different set of bolus time intervals are determined by day of week, to accommodate, for example, different bolus patterns during weekends versus weekdays.

39 Claims, 10 Drawing Sheets

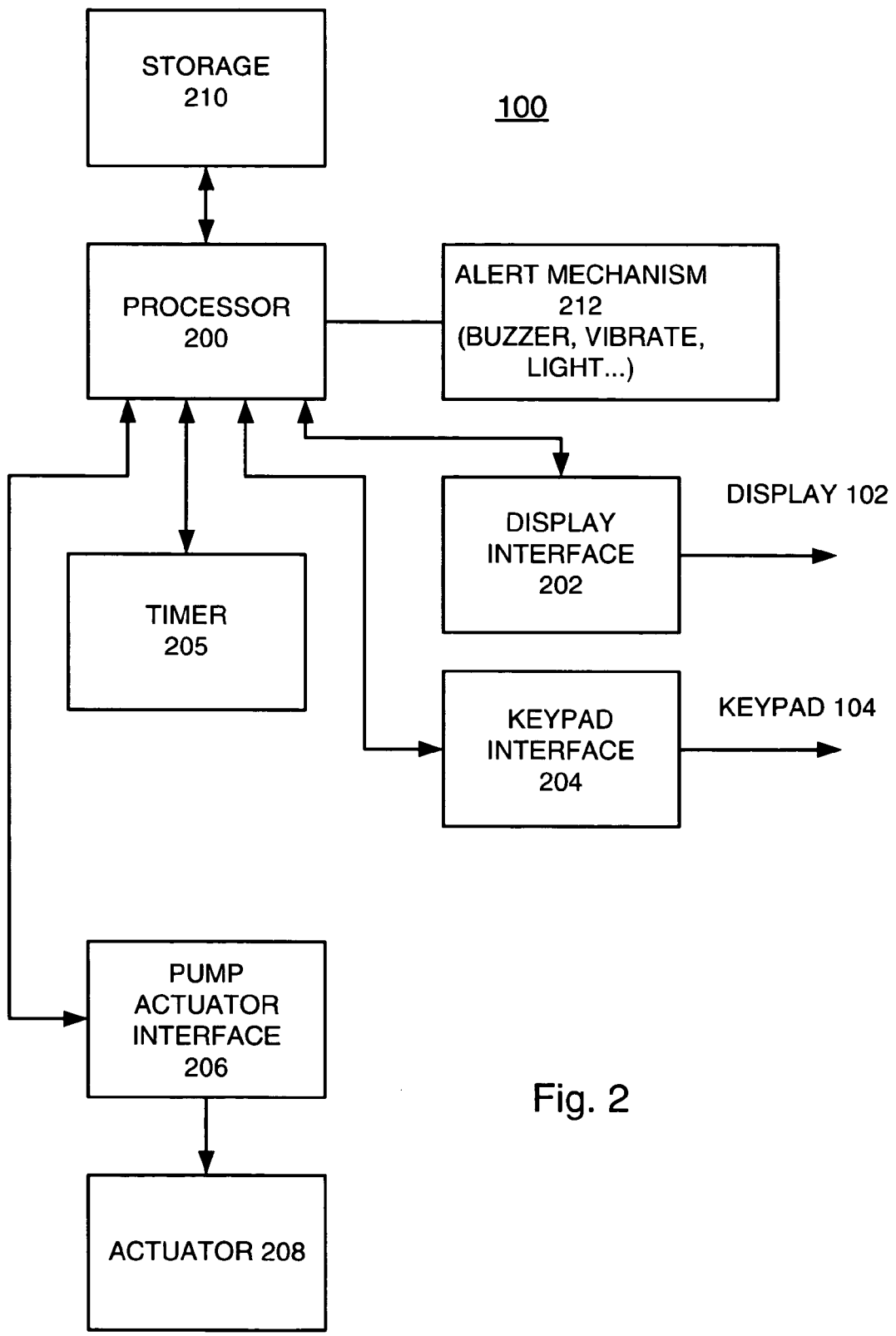

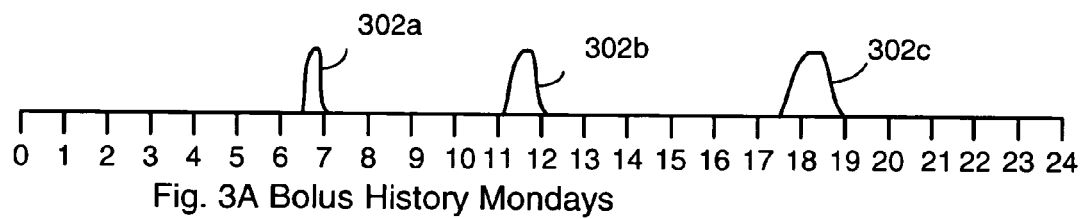
Fig. 3A Bolus History Mondays
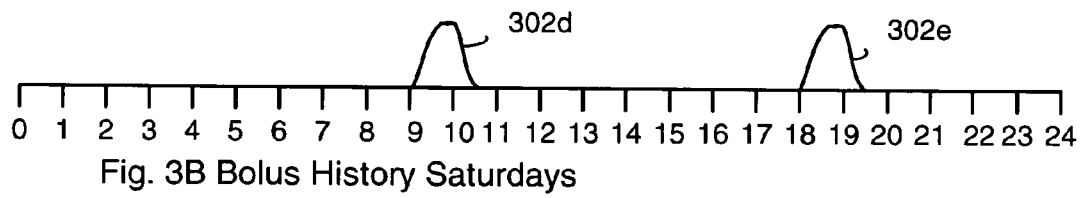
Fig. 3B Bolus History Saturdays
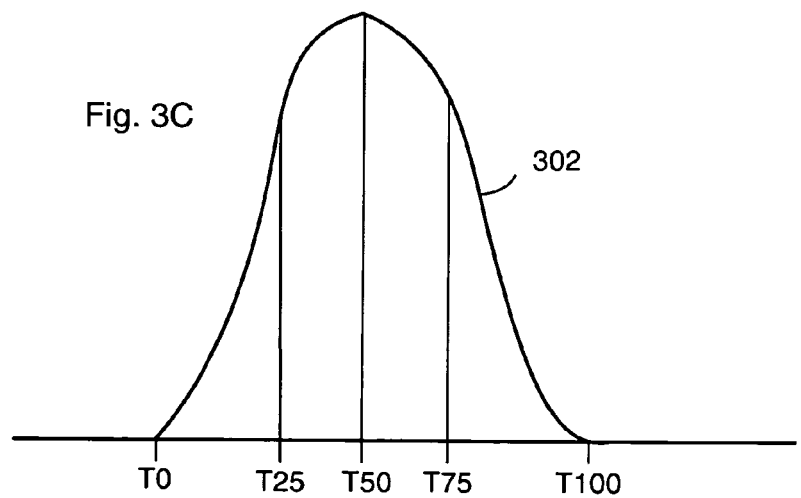
Fig. 3C

BOLUS TIME TABLE 252

| ADDRESS | BOLUS TIMES | TIME INTERVAL GROUP |
|---|---|---|
| 00000 | TIME1 | 1 |
| 00001 | TIME2 | 1 |
| 00010 | TIME3 | 1 |
| 00011 | TIME4 | 2 |
| 00100 | TIME5 | 2 |
| | ● ● ● | |
| 11110 | TIME31 | 5 |
| 11111 | TIME32 | 6 |

Fig. 5B

BOLUS TIME TABLE 252

| BOLUS TIMES | TIME INTERVAL GROUP |
|---|---|
| TIME1 | 1 |
| TIME2 | 1 |
| TIME3 | 1 |
| TIME4 | 2 |
| TIME5 | 2 |
| ● ● ● | |
| TIME31 | 5 |
| TIME32 | 6 |

↑ BOLUS TIME INPUT    ↑ TIME INTERVAL GROUP INPUT

Fig. 5C

MEDICAL INFUSION PUMP CAPABLE OF LEARNING BOLUS TIME PATTERNS AND PROVIDING BOLUS ALERTS

BACKGROUND OF THE INVENTION

1. Field of the Invention

The current invention generally relates to medical infusion pumps. In particular, the current invention is especially applicable to insulin pumps.

2. Description of the Related Art

Various medical infusion pumps are commercially available. A medical infusion pump infuses a medicament into a living body according to a programmed rate(s) for background (basal) doses of the medicament, and user initiated bolus doses. Insulin pumps, for example, are widely used by diabetics. To achieve the best control of diabetes, many diabetics are turning to the use of insulin pumps. An insulin pump is a device that periodically dispenses very small amounts of insulin (or suitable insulin analogs) according to a preprogrammed profile set by the user to cover basal insulin needs. Basal insulin takes care of or "covers" glucose produced by the body on a continuous basis. When a diabetic person consumes food, the diabetic person needs to estimate the amount of insulin required to cover the carbohydrates, and perhaps other food components such as protein, and program the pump to administer a bolus amount of insulin sufficient to cover the food. Typically, many insulin pump users compute the amount of carbohydrates in the food, and, using an individual carbohydrate/insulin ratio, calculate the magnitude of the bolus. For example, if known for a particular individual that one unit of insulin covers 10 grams of carbohydrates, and the meal has 100 grams of carbohydrates, the individual would program the pump to administer a bolus of 10 units of insulin. Because the bolus amount varies per meal and the diabetic person may skip a meal, an insulin pump is not preprogrammed to administer a bolus amount of insulin.

It is quite easy for a diabetic person to fail to program a bolus at mealtime. The failure to program the bolus can be either a lapse of memory or an error, such as not pushing a key on the insulin pump's keypad hard enough. If the bolus is not administered, blood sugar levels typically will rise to unhealthy and perhaps dangerous levels. Even if the person feels the high blood sugar effects, by then some harm or risk for diabetic complications have occurred. Usually a diabetic does not sense high blood glucose until the blood glucose concentration is above 400 mg/dl, whereas the usual target range for blood glucose concentration is 70 mg/dl to 120 mg/dl. While one could take more frequent blood sugar readings with available blood testing equipment, such testing is expensive and painful.

Existing medical infusion pump art includes U.S. Pat. No. 6,650,951 B1, "Method and Insulin Pump for Providing a Forgotten Bolus Warning", which allows a user to program intervals during which boluses are expected. That is, mealtimes are entered (or defaulted), and wait times are entered (or defaulted). If a bolus is not taken between the mealtime and the mealtime plus the wait time, a warning (audio, tactile, visual) is issued. However, this invention requires programming by the user, and therefore remains susceptible to errors by the user, e.g., lack of programming by the user or incorrect programming by the user.

A need exists for a medical infusion pump that does not require the user to program expected bolus times into the medical infusion pump, but still provides one or more alerts corresponding to time intervals during which boluses are normally taken by a user.

SUMMARY OF THE INVENTION

The current invention teaches methods and apparatus to "learn" when a user of a medical infusion pump takes his or her boluses, and alert the user at a time or times associated with a bolus time interval when it is likely that a bolus should be taken, given the user's historical pattern of taking boluses.

In an embodiment, the medical infusion pump determines one or more bolus time intervals during which a bolus is usually taken, and, if a bolus is not taken during an active bolus time interval in the one or more bolus time intervals, an alert mechanism is activated. An active bolus time interval is a particular bolus time interval in the one or more bolus time intervals when a current time (e.g., 6:00) is within the particular bolus time interval (e.g., 5:50 to 6:30), or, as will be explained below, is within a predetermined anticipatory period prior to an earliest bolus time in the particular bolus time interval, or within a predetermined wait time after a latest bolus time in the particular bolus time interval. A particular bolus time interval is therefore widened by the predetermined anticipatory period (if implemented) and the predetermined wait period (if implemented).

In an embodiment, the medical infusion pump determines that a current time is approaching a particular bolus time interval and alerts the user that a bolus is likely to be needed soon. A predetermined anticipatory period is provided by default or by a user override to specify how long before an earliest bolus time in the bolus time interval the alert should be activated.

In another embodiment, the medical infusion pump alerts the user if a bolus has not been taken prior to the latest bolus time in a particular bolus time interval, and a bolus has also not been taken during a predetermined wait time after the latest bolus time in the particular bolus time interval.

In another embodiment, when a timer determines that the current time has entered a particular bolus time interval during which a bolus is usually taken, the medical infusion pump will activate an alert mechanism at one or more calculated alert times associated with the particular bolus time interval. For example, the alert mechanism is activated when the current time is at the beginning of the particular bolus time interval; activated again at a current time equal to a calculated alert time when, 25% of the time, for the particular bolus time interval, a bolus has been taken prior to that calculated alert time. The alert mechanism activated again when the current time is equal to a calculated alert time when, 50% of the time, for the particular bolus time interval, a bolus has been taken prior to that calculated alert time. The alert mechanism is activated again when the current time is equal to a calculated alert time when, 75% of the time, a bolus has been taken prior to that calculated alert time. The alert mechanism is activated again when the current time is equal to a calculated alert time that is the end of the end of the particular bolus time interval, based upon the user's history of taking boluses.

In an embodiment, the medical infusion pump includes a storage. More than one time interval groups are stored in the storage. A time interval group is a period of time when bolus patterns are similar for most occurrence of when a current time is within the time interval group. Each of the more than one time interval groups is capable of storing one or more bolus time intervals. A processor in the medical infusion pump determines, using the user's history of boluses delivered by the medical infusion pump in each of the more than one time interval groups, the one or more bolus time intervals during which a bolus is usually taken by the user in each of the more than one time interval groups, and, activates an alerting mechanism at one or more time points associated with the one or more bolus time intervals.

In an embodiment, the medical infusion pump uses a separate time interval group for each day of the week, and considers the user's bolus history by day of the week, thus accommodating different bolus patterns by day of the week.

In another embodiment, the medical infusion pump uses a first time interval group for weekdays (i.e., Monday, Tuesday, Wednesday, Thursday, and Friday), a second time interval group for Saturday, and a third time interval group for Sunday, to accommodate weekday patterns which are similar for many users; Saturday patterns, and Sunday patterns. For many users, Saturday and Sunday bolus patterns differ, so that separate time interval groups are used for Saturday and Sunday.

In a method embodiment, a method of alerting a user of a medical infusion pump that the user has not yet taken a bolus during a bolus time interval determined by the user's history of taking boluses is disclosed, comprising the steps of: storing, in the medical infusion pump, time information at which boluses are taken by the user; determining, by the infusion pump, one or more bolus time intervals during which a bolus is usually taken by the user, using the time information; calculating one or more calculated alert times, using the time information; and alerting the user if a bolus has not yet been taken prior to the one or more calculated alert times.

BRIEF DESCRIPTION OF THE DRAWINGS

FIG. 2 is a block diagram of the components of the medical infusion pump.

FIG. 3A shows a chart of bolus patterns for an exemplary Monday.

FIG. 3B shows a chart of bolus patterns for an exemplary Saturday.

FIG. 3C shows a detailed drawing of frequency of boluses during an identified bolus time interval, highlighting the $0^{th}$, $25^{th}$, $50^{th}$, $75^{th}$, and $100^{th}$ percentile probability times for the bolus time interval.

FIG. 5B shows a bolus time table implemented as a linearly addressed storage.

FIG. 5C shows a bolus time table implemented as a physical FIFO (first in first out) structure.

DETAILED DESCRIPTION OF THE PREFERRED EMBODIMENTS

The invention will be described in detail with reference to the figures. It will be appreciated that this description and these figures are for illustrative purposes only, and are not intended to limit the scope of the invention. In particular, various descriptions and illustrations of the applicability, use, and advantages of the invention are exemplary only, and do not define the scope of the invention. Accordingly, all questions of scope must be resolved only from claims set forth elsewhere in this disclosure.

The current invention teaches methods and apparatus embodied in a medical infusion pump to "learn" when a user of the medical infusion pump takes his or her boluses, and alert the user at a calculated alert time or times when it is likely that a bolus should be taken but has not yet taken, given the user's historical pattern of taking boluses.

For purposes of illustration, the invention is described with reference to an insulin pump, which is one example of a medical infusion pump; however, any medical infusion pump is within the spirit and scope of the invention.

Figure 1:
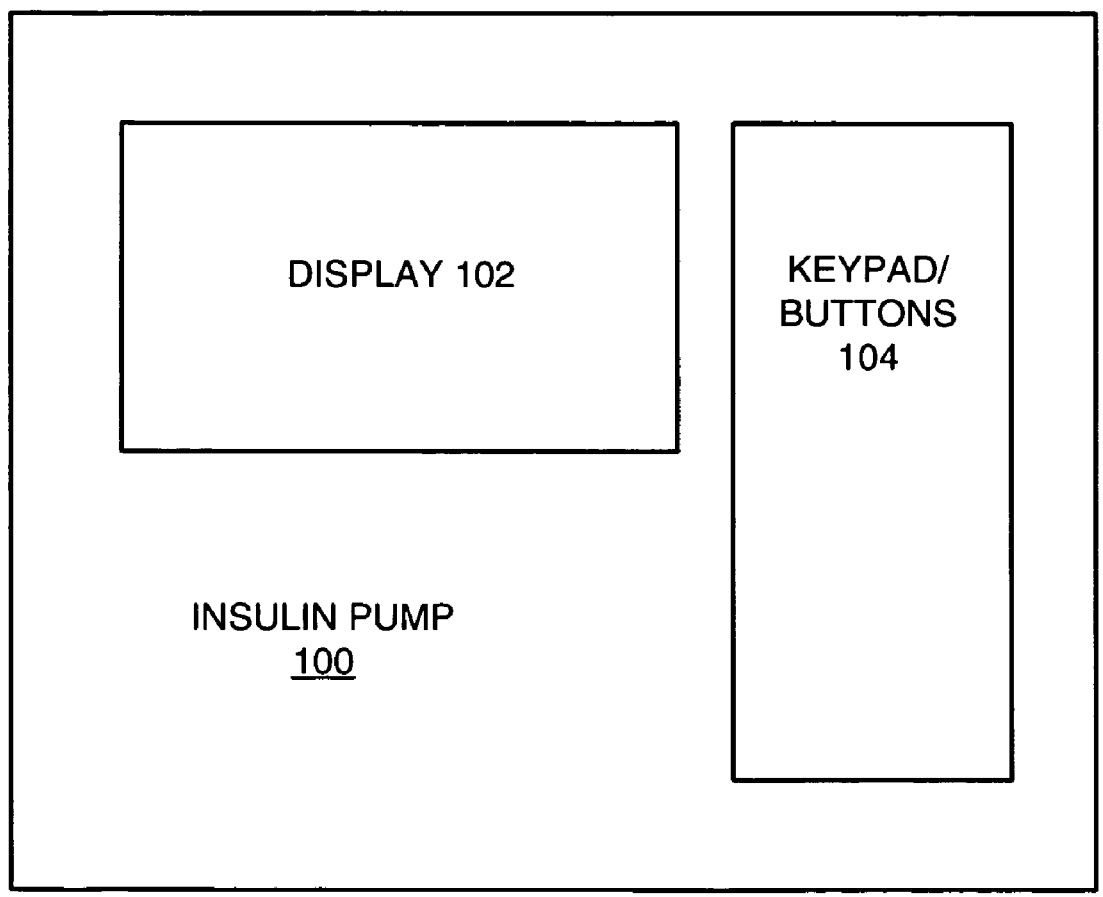
FIG. 1 is a schematic drawing of a medical infusion pump.

Having reference now to the drawings, in FIG. 1, there is shown an exemplary insulin pump of the preferred embodiment generally designated by the reference character 100. As shown in FIG. 1, insulin pump 100 includes a display 102 for viewing by a user and a keypad 104 for receiving user entries. Some insulin pumps 100 also have a computer interface (not shown) for sending data to, or receiving data from, a computer.

Referring to FIG. 2, there is shown a block diagram representation illustrating the insulin pump 100 for implementing methods for providing one or more bolus alerts for an insulin pump in accordance with the preferred embodiment. Insulin pump 100 includes a processor 200 coupled to a display interface 202 which is coupled to display 102. Processor 200 is coupled to a keypad interface 204 which is coupled to keypad 104. Processor 200 is coupled to a pump actuator interface 206 which is coupled to an actuator 208 suitable for delivering insulin doses (medical infusion pumps other than insulin pumps will deliver doses of other medicament). Processor 200 is coupled to a storage 210 that provides program and data storage. Storage 210 is constructed of any combination of volatile and/or nonvolatile storage suitable for a particular embodiment. Processor 200 is coupled to an alert mechanism 212, that, in various embodiments is a buzzer, a vibrator, a light emitting diode, or the like, suitable for providing audible, tactile, or visual alerts to an insulin pump user. Processor 200 is coupled to a timer 205. Advantageously, timer 205 is capable of maintaining a current time, including time of day and day of the week (i.e., Monday, Tuesday, Wednesday, Thursday, Friday, Saturday, or Sunday). Any suitable format for time of day is contemplated by the present invention. For example, "24 hour time", or "military time" avoids "AM" and "PM". In "military time", 03:15 is three hours and 15 minutes past midnight. 17:30 is 17 hours and 30 minutes past midnight. Alternatively, "AM/PM" time is used, with the prior two examples translating to 3:15 AM and 5:30 PM. Medical infusion pumps that are used to produce boluses in time units other than time of day and day of week are contemplated.

Processor 200 is suitably programmed to execute the steps of the flow chart of FIG. 9, which will be described later.

Referring now to FIG. 3A, a user's bolus history for "Mondays" is shown. Insulin pump 100 has established a first bolus time interval from 06:30–07:00 by "learning" when the user historically takes boluses during "Mondays". Distribution 302a is a histogram of bolus doses taken during the first bolus time interval, and indicates how many boluses are taken at times within the first bolus time interval. Distribution 302a shows that no boluses have been taken prior to 06:30, most boluses in the first bolus time interval are taken approximately 06:45, and no boluses are taken after 07:00. A diabetic normally takes a fast acting insulin (or insulin analog) at a meal or shortly before a meal. The exemplary distribution 302a represents a typical breakfast bolus pattern for a diabetic, who eats breakfast at approximately the same time every Monday. Distribution 302b, similarly shows a typical Monday "lunch meal bolus" distribution for the user, during a second bolus time interval. The user historically takes a bolus between approximately 11:00 and 12:00 on Mondays. Distribution 302c shows a typical Monday "dinner meal bolus" for the user, who historically takes a dinner bolus during a third bolus time interval of between approximately 17:30 and 19:00. The exemplary widths of the three bolus time intervals are reasonably typical, and show the typically wider bolus time intervals for lunch and dinner, since many people have more variability in when they eat lunch and dinner than breakfast. It is to be understood that the actual widths of any particular bolus time interval is determined by the medical infusion pump, using the user's history of taking boluses. For example, if the user has a history of eating at substantially the same time for dinner on Mondays, the width of the Monday dinner bolus time interval will be narrow.

FIG. 3B shows an example of a diabetic's bolus history for "Saturdays". The user in the example historically boluses only twice a day, accommodating a brunch between approximately 09:00 and 10:30, shown as distribution 302d, and a dinner between approximately 18:00 and 19:30, shown as distribution 302e.

The examples of FIGS. 3A and 3B are meant to illustrate that a user's bolus patterns can and do differ by day of the week. For many people, bolus patterns are similar from one weekday to another weekday; that is, Mondays through Fridays can be considered one time interval group. For other people, each day may be different, and each day should be considered as a time interval group.

FIG. 3C shows an exemplary general distribution 302 corresponding to a user's historical frequency of bolus events during an exemplary bolus time interval. The shape of the distribution is shown as "bell shaped", but could be of any shape. T0 represents the zeroth percentile of distribution 302; that is, no bolus in the time interval of distribution 302 is earlier than the time T0. 25% of boluses in the time interval of distribution 302 have occurred by time T25. 50% of boluses in the time interval of distribution 302 have occurred by time T50. 75% of boluses in the time interval of distribution 302 have occurred by time T75. 100% of boluses in the time interval of distribution 302 have occurred by time T100. Although the zeroth, $25^{th}$, $50^{th}$, $75^{th}$, and $100^{th}$ percentiles are used for exemplary purposes, any percentile value(s) are contemplated, as well as any other measure of where the current time is within, prior to, or even after, a particular bolus time interval. With knowledge of the characteristic of the particular distribution 302, infusion pump 100 can provide the user with alerts at calculated alert times associated with the particular distribution 302, using alert mechanism 212. A calculated alert time is a time associated with an active bolus time interval at which an alert is activated if a bolus has not yet been taken during the active bolus time interval. An active bolus time interval is a particular bolus time interval in the one or more bolus time intervals when a current time (e.g., 6:00) is within the particular bolus time interval (e.g., 5:50 to 6:30), or, as will be explained below, is within a predetermined anticipatory period prior to the beginning of the particular bolus time interval, or within a predetermined wait time after the particular bolus time interval.

For example, a calculated alert time can be calculated to be at time T0 of distribution 302, triggering an alert by alerting mechanism 212, alerting the user to the fact that a bolus is expected "soon". In a buzzer embodiment of alert mechanism 212, for example, a single soft beep (or other characteristic sound) may be issued at T0. Similarly, when the current time is at a calculated alert time at T25, a second alert is issued if a bolus has not yet been taken. Alerts are similarly issued at calculated alert times corresponding to T50, T75, and T100. In embodiments, the loudness of the beeps (or intensity of vibration, etc, depending on the type of alert mechanism embodied) increases at each such increasing percentile. In embodiments, multiple beeps (or vibrations, etc, depending on the type of alert mechanism embodied) are issued at each such increasing percentile.

The invention further contemplates a calculated alert time following the end of distribution 302. For example, Medical infusion pump 100 calculates a calculated alert time equal to the end of distribution 302 plus a predetermined wait time. If no bolus has been taken during exemplary distribution 302 or within the predetermined wait time (e.g., 30 minutes) after the end of distribution 302 (i.e., the calculated alert time), alert mechanism 212 is activated. The predetermined wait time is stored in a control data 259 as will be described later.

Furthermore, an alert mechanism 212 can be activated at a calculated alert time prior to the beginning of a particular distribution 302. For example, in an embodiment, if the particular distribution 302 begins at 18:00, and a predetermined anticipatory period is ten minutes, the alert mechanism 212 is activated at calculated alert time 17:50 (that is, the beginning of the bolus time interval corresponding to the particular distribution 302). The predetermined anticipatory period is stored in control data 259, which will be discussed later.

Figure 4:
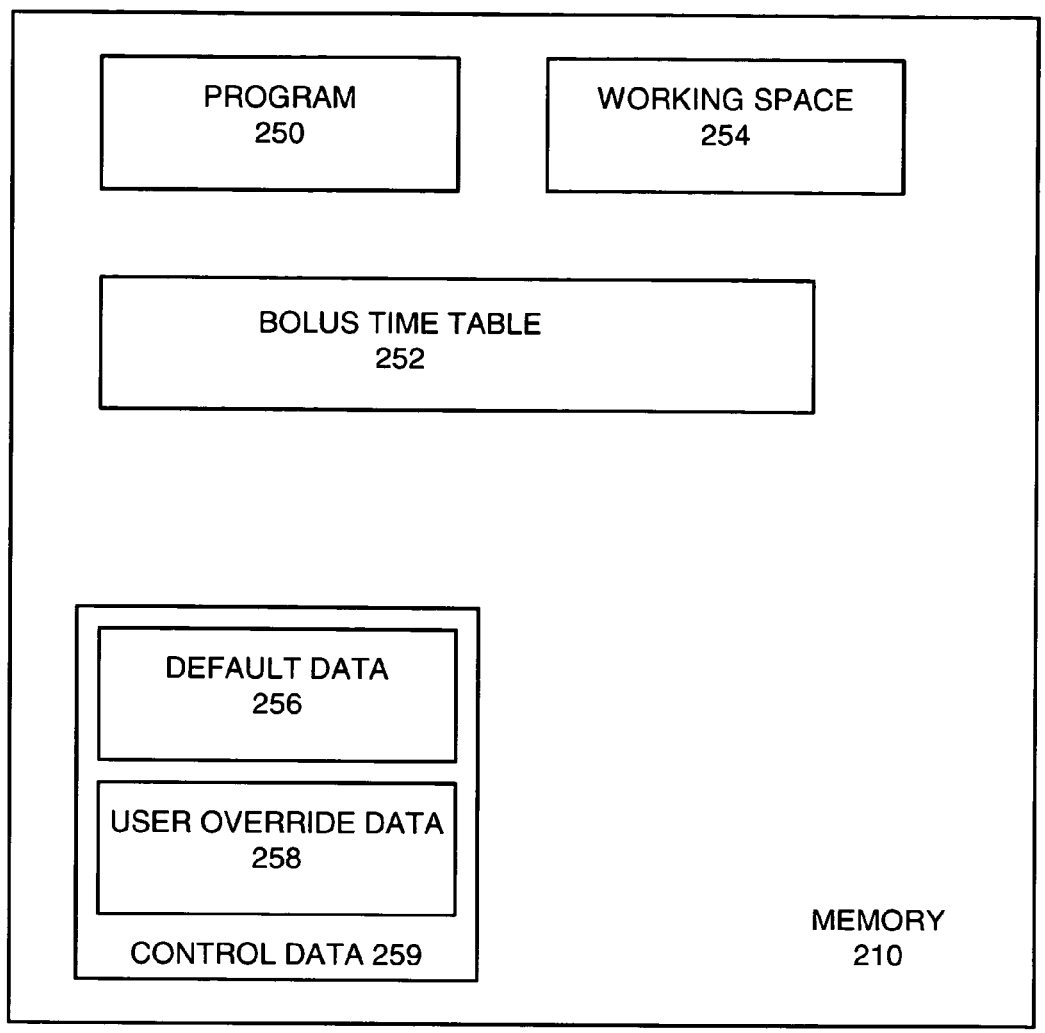
FIG. 4 is a block diagram showing contents of a memory of the medical infusion pump.
Figure 6:
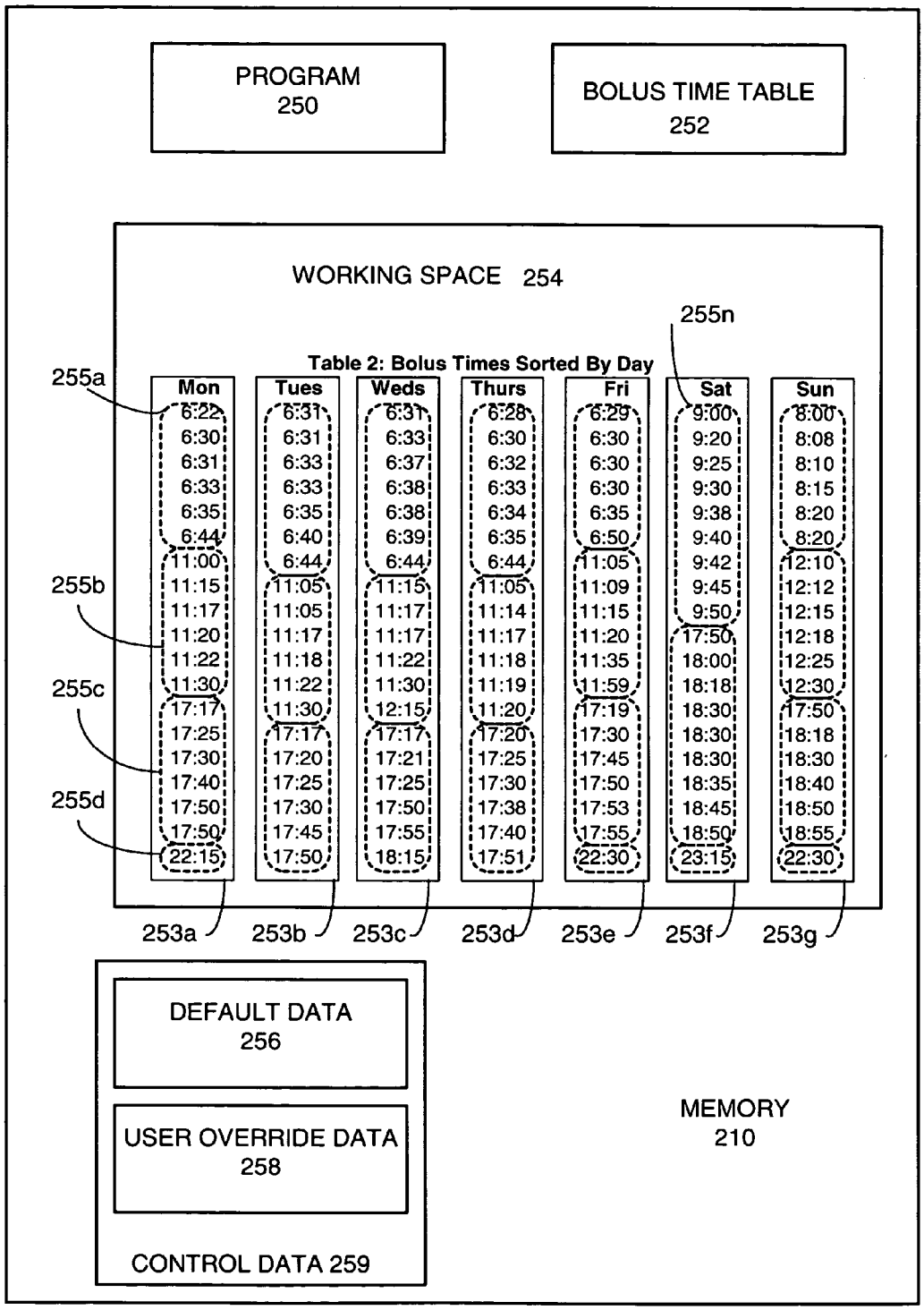
FIG. 6 is a block diagram of a working space in the memory of the medical infusion pump, identifying bolus time intervals within time interval groups.
Figure 7:
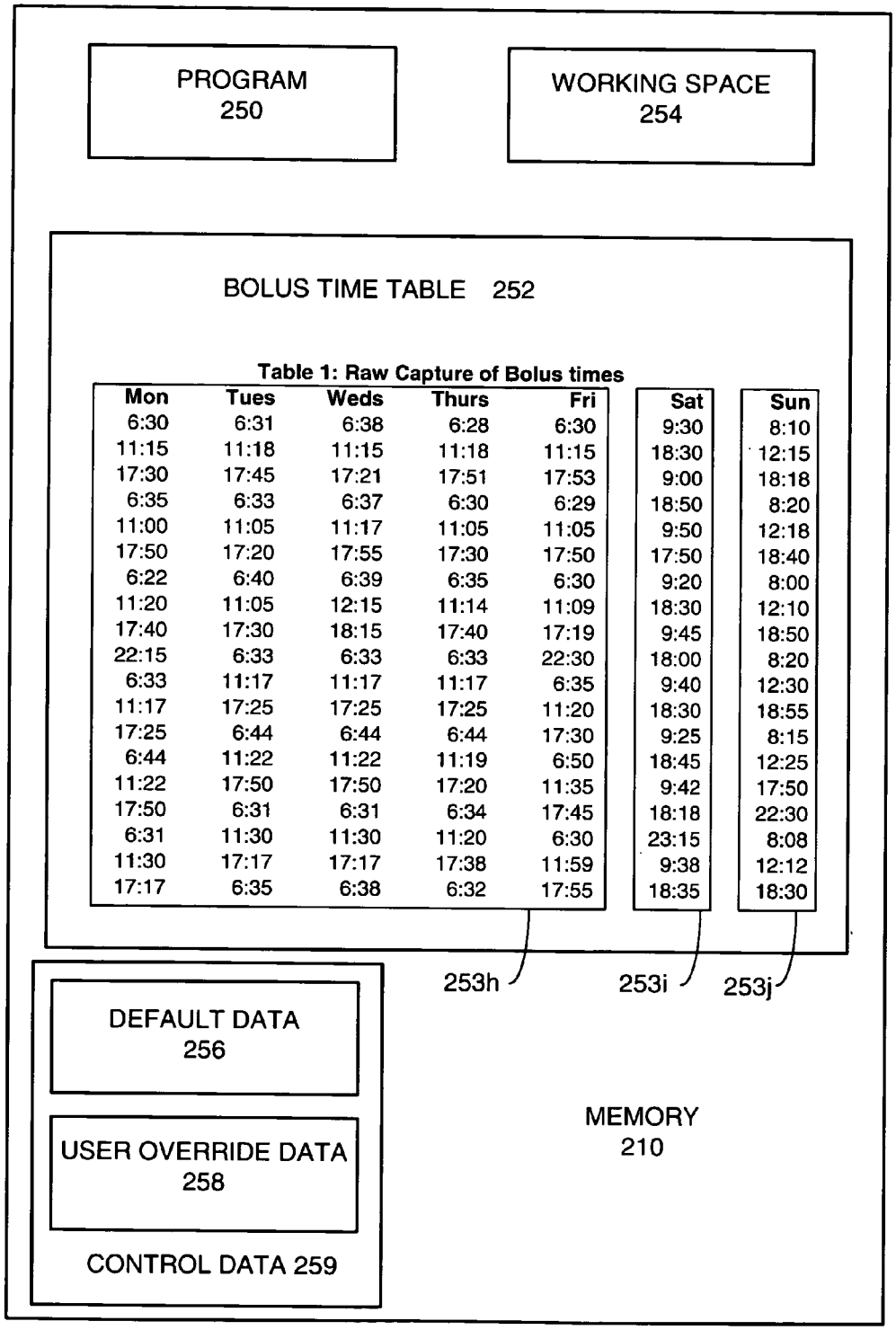
FIG. 7 is a block diagram of a bolus time table in the memory of the medical infusion pump, with weekdays all lumped into a first time interval group in the bolus time table, Saturday being a second time interval group, and Sunday being a third time interval group.

FIG. 4 shows an exemplary memory usage of storage 210. A program 250, suitable for execution by processor 200 (shown in FIG. 2) resides in storage 210. Program 250 is advantageously stored in nonvolatile storage, such as ROS (Read Only Storage), Flash memory, FeRAM (Ferroelectric Random Access Memory), or other suitable nonvolatile storage. Nonvolatile storage is preferable for storage of program 250 to ensure that the contents of program 250 are not lost if power is lost (e.g., during battery changes in infusion pump 100 (batteries not shown)). A bolus time table 252 is used to store times at which infusion pump 100 delivers boluses. Examples of bolus time tables 252 are shown in FIGS. 5, 6, 7 and will be discussed later. Bolus time table 252 is advantageously stored in nonvolatile storage.

Those skilled in the art will recognize that volatile storage such as SRAM (static random access memory), or DRAM (dynamic random access memory) that has a supply voltage "backed up" by a suitable capacitor or other means (e.g., a separate battery) is to be considered functionally equivalent to a nonvolatile storage. Such "backed up" volatile storage is considered to be nonvolatile storage.

Control data 259 includes data that is used by program 250 to identify bolus time intervals and to define time interval groups. Control data 259 includes default data 256 and user override data 258.

Default data 256 includes information provided by the manufacturer of infusion pump 100. In an embodiment, default data 256 may include a default definition of time interval groups in a bolus time table logical partition information. A time interval group is a recurring period of time in which bolus patterns during the period of time are similar. For example, if a user of an insulin pump eats breakfasts, lunches, and dinners at approximately the same times every Monday, Mondays could be defined as a time interval group. In an embodiment, the bolus time table logical partition information defines each day of the week as a separate time interval group. In an alternate embodiment, the bolus time table logical partition information defines weekdays as a first time interval group; Saturdays as a second time interval group; and Sundays as a third time interval group. Any recurring period of time in which bolus patterns are similar are contemplated as a particular instance of a time interval group.

In an embodiment, default data 256 includes a minimum considerable bolus that defines a magnitude of a bolus eligible to be entered into a bolus time table (see examples data in a bolus time table in FIG. 5A) is defined. Boluses smaller than the minimum considerable bolus are not entered into the bolus time table. A diabetic may take a small "correction bolus" between meals, typically respondent to a postprandial blood glucose reading that is higher than desired. For example, if the diabetic's blood glucose reading is 40 mg/dl higher than desired at a time between meals, and the diabetic's insulin sensitivity is such that one unit of insulin causes a 40 mg/dl decrease in blood glucose, the diabetic would program the infusion pump to deliver a one unit bolus. However, the diabetic would not typically want the medical infusion pump to alert him or her to missing such a "correction bolus". Therefore, the manufacturer would provide a default minimum considerable bolus of perhaps two units; in which case any bolus less than two units would not be entered into the bolus time table.

A maximum bolus time interval duration is stored in default data 256. The maximum bolus time interval duration is used to define a maximum time period to be considered in determining bolus time intervals, as will be discussed in more detail later.

User override data 258 contains user specified overrides to corresponding data in default data 256. (In an embodiment, however, default data 256 is not implemented, in which case, all data described in default data must have a user override data value entered in user override data 258). The user enters such overrides using the keyboard, or via a computer interface (not shown) that some medical infusion pumps provide. For example, if default data 256 defines a separate time interval group for each day of the week, but a user wishes to change that definition to define a first time interval group that includes all weekdays (knowing that for him or her, the meal times don't vary by day during a week); a second time interval group defined as Saturdays, and a third time interval group defined as Sundays, the user simply enters his or her overrides into user override data 258, and those overrides will be used instead of the corresponding information in default data 256. User override data 258 is advantageously stored in nonvolatile storage.

Working space 254 is storage that is accessed and used by processor 200 to manipulate data. Working space 254 can be thought of as a "scratchpad" memory, and may be implemented in either volatile or nonvolatile storage.

Figure 5A:
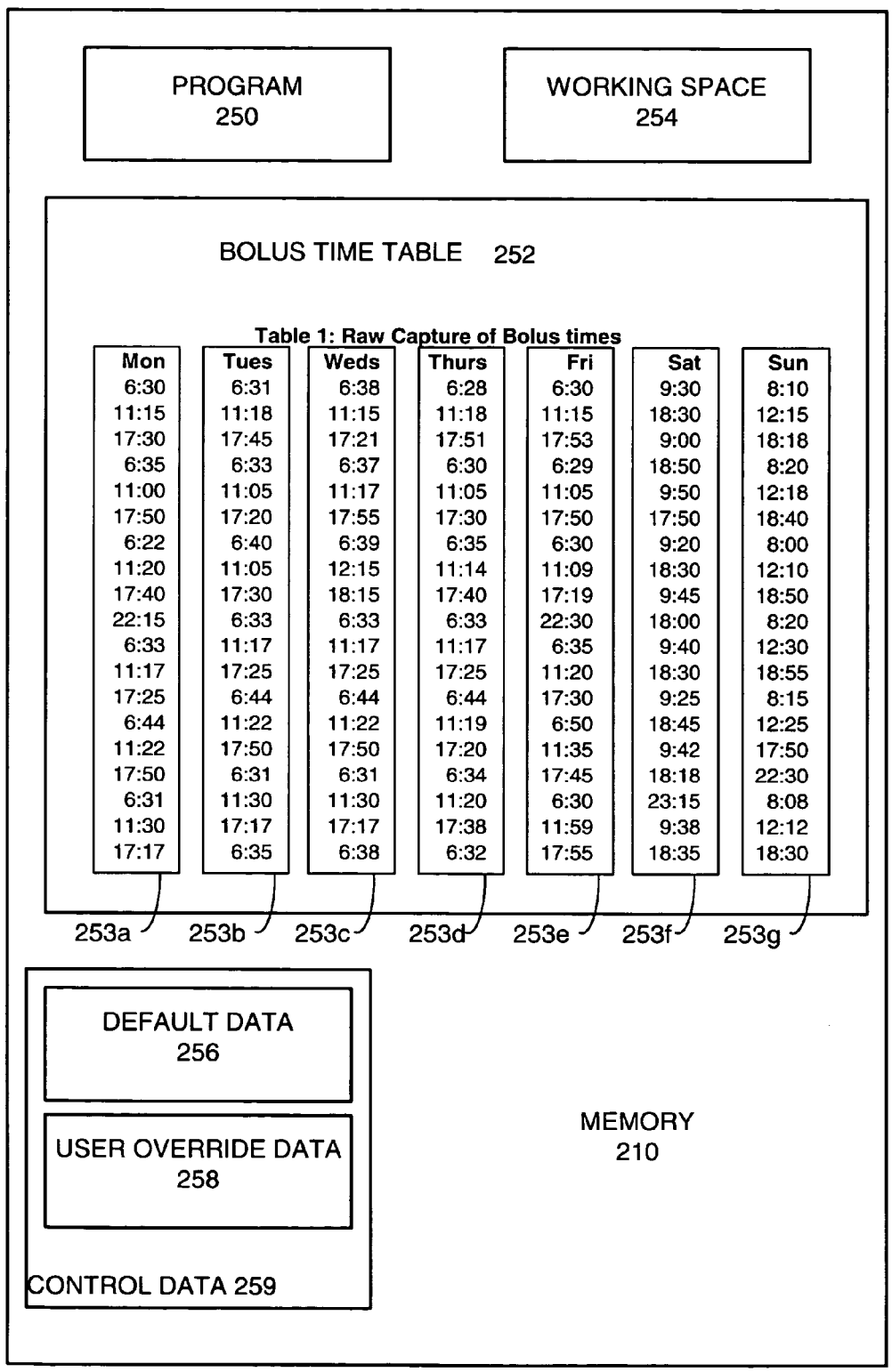
FIG. 5A is a block diagram with exemplary data stored in a bolus time table in the memory of the medical infusion pump. Each day of the week is shown as a separate time interval group in the bolus time table.

FIG. 5A shows an exemplary bolus time table 252 in memory 210. Time interval groups 253a–253g are defined in bolus time table 252; a separate time interval group defined for each day of the week. In the exemplary embodiment of FIG. 5A, data in a time interval group is handled as a FIFO (first in first out) buffer. In the example shown, and considering time interval group 253a (i.e., Mondays), the most recent bolus was taken at 17:17; the prior bolus was taken at 11:30. The "oldest" bolus data for time interval group 253a is 6:30, the topmost number in time interval group 253a. Since time interval group 253a operates logically as a FIFO, when another bolus is taken on a Monday, the "6:30" (oldest bolus time) is discarded and the new bolus time is added under the "17:17" time. Bolus time table 252 is shown to provide 19 bolus times in each time interval group. Any number of bolus times in a bolus time table or a time interval group is contemplated. However, advantageously, provision for a number of boluses for at least several days' worth of data is made in order that enough bolus time information is available to establish, with some confidence, bolus time intervals during which boluses are normally taken. A particular bolus time interval begins at a beginning bolus time interval time corresponding to the beginning of a particular distribution (e.g., distribution 302), and the particular bolus time interval ends at an ending bolus time interval time corresponding to the ending of the particular distribution (e.g., distribution 302). Note that, as described before, for embodiments including the predetermined anticipatory time and the predetermined wait time, the width of the particular bolus time interval is correspondingly broadened.

Advantageously, default "null" values are initialized into bolus time table 252, and provision is made to allow all values to be "nulled" by the user. A null value for a time is ignored by program 250 in determining bolus time intervals. The provision to allow the user to "null" the bolus time table accommodates, for example, the possibility that the user transfers the infusion pump to a different user. The operation of adding and discarding bolus times into a time interval group has been described as a FIFO operation.

Those skilled in the art will understand that time interval groups need not be physically embodied as a FIFO register stack. For example, in an embodiment, the one or more time interval groups are stored in a storage array, with suitable pointers keeping track of "fronts" and "ends" of logical FIFOs. Memory arrays, rather than physical FIFOs also facilitate accommodation of overrides and changes in how time interval groups are defined. FIG. 7, to be discussed later, shows a different definition of time interval groups for exactly the same data of FIG. 5A, and therefore allows the user to change definition of time interval groups at any time, without having to wait for new valid bolus times to provide enough data for good confidence in identifying bolus time intervals within the time interval groups. Advantageously, three or four bolus times occurring within a time period equal to or less than the maximum bolus time interval duration are used to identify each instance of a bolus time interval. Additional bolus times add confidence that a particular bolus time interval is well defined. However, the invention contemplates even a single bolus time in the particular bolus time interval.

It will be understood by those skilled in the art that although bolus time table 252 is shown for exemplary purposes as having physical columns by day of week (which could be other time delineators in other medical infusion pumps, for which appropriate time delineators might be hours, or months), there is no need for the physical implementation to have physical columns. For example, in an embodiment shown in FIG. 5B, the entire bolus time table 252 is implemented in a linearly addressed memory, each memory element (i.e., row or word) addressed containing a bolus time and a time interval group identifier having information as to the time interval group to which that memory element is currently assigned. In another alternative embodiment shown in FIG. 5C, bolus table 252 is implemented as a single FIFO, each element of which contains a bolus time and a time interval group identifier. In the physical FIFO of FIG. 5C, whenever a bolus occurs the time of the bolus and the associated time interval group are input at an input end of the FIFO. The bolus time and associated time interval group at the opposite end of the FIFO are discarded. In alternative embodiments of the bolus time tables 252 of FIGS. 5B and 5C, only the times, including day of week, (or other appropriate times for a particular type of medical infusion pump) are stored, with identification of time interval groups and bolus time intervals being done in working space 254 as described below.

FIG. 6 shows an embodiment of working space 254 in memory 210 that is used to simplify identification of bolus time intervals; identification of when the current time has entered a particular bolus time interval; and identification of where, in a particular time interval the current time is, relative to calculated alert times (e.g., the T0, T25, T50, T75, T100 times as discussed earlier, although other measures of progression through a particular bolus time interval are contemplated). Working space 254 has a copy of bolus time table 252, with bolus times sorted in each time interval group, or, at least, an active time interval group, where the active time interval group is the interval group under consideration for the present day, in the example. Whenever a bolus is taken, bolus time table 252 is updated, and a copy of the updated bolus time table 252 is made to working space 254.

In the example of FIG. 6, if the current day is Monday, only time interval group 253a need be sorted. Once sorted, the times in each time interval group become more easily used. For example, bolus time interval 255a (e.g., the boluses corresponding to the user's Monday breakfasts) is easily identified. Assuming a maximum bolus time interval duration value of two hours, the six bolus times of bolus time interval 255a are readily identified in sorted time interval group 253a as a group of bolus times clustered within a time period defined by the maximum bolus time interval duration. The bolus times in bolus time interval 255a make up a distribution of times, such as exemplary distribution 302. Bolus time interval 255a has an earliest time at 6:22. In an embodiment wherein a calculated alert time is the earliest time in the bolus time interval, the user is alerted (by alert mechanism 212) at 6:22, reminding the user that a bolus is likely to be needed then, or in the near future.

Bolus time intervals in FIG. 6 are enclosed in dotted lines with curved corners; for simplicity and clarity in the figure, only bolus time intervals 255a, 255b, 255c, 255d, and 255n are explicitly identified with reference numerals. Knowing the number of bolus times, and the values of the bolus times, in a bolus time interval, alerts can be activated at any calculated alert time or times. In an embodiment, processor 200 computes the average of the bolus times in a bolus time interval as a calculated alert time and activates the alert mechanism when the current time equals the calculated alert time if a bolus has not yet been taken during the active bolus time interval. In the exemplary bolus time interval 255a, the average bolus time (exemplary calculated alert time) is 6:30 (rounded up to the nearest minute). Other, or alternative, calculated alert times to activate alerts in bolus time interval 255a, or other bolus time intervals, such as 255n, are contemplated. The present invention also contemplates a calculated alert time suitable for activation of alert mechanism 212 after a predetermined wait time after the latest bolus time in a bolus time interval. The value of the predetermined wait time is provided in default data 256 and/or in user override data 258. In the case of an insulin pump, the predetermined wait time should be defaulted to not more than about an hour in order that the insulin pump user's blood glucose concentration does not rise to extremely high levels if the user, in fact, did have a meal during the just expired bolus time interval and failed to take a bolus.

Another advantage of sorting by time of day in a time interval group, e.g., 253a, is to facilitate management of bolus time intervals, e.g., 255a, 255b, 255c, and 255d, within the time interval group. Information in control data 259 is used by program 250 to identify bolus time intervals within time interval groups. The maximum bolus time interval duration is read from control data 259. Program 250 examines a time interval group such as 253a, looking for a number of bolus times occurring within the maximum bolus time interval duration. Advantageously, the maximum bolus time interval duration is wide enough to identify likely bolus time intervals, but not wide enough to introduce ambiguity between likely bolus periods, thereby allowing program 250 to distinguish a first bolus time interval from a second bolus time interval. For example, a diabetic typically has three meals a day, and may have a bedtime snack. Meals are typically four to six hours apart. Meals typically occur within two hours of the same time during a time interval group. Considering these factors, the maximum bolus time interval duration could be written into default data 256 as two hours. By scanning the bolus times in time interval 253a, while considering the maximum bolus time interval, program 250 readily identifies bolus time intervals 255a, 255b, 255c, and 255d. Note that there may have been small correction boluses taken that were rejected as being smaller than the minimum considerable bolus described earlier, and are therefore not recorded in bolus time table 252.

For embodiments of bolus time table 252 as shown in FIGS. 5B and 5C, but without the optional time interval group field as shown, the bolus times (i.e., TIME1–TIME32), which include day of week in these embodiments, bolus time table is copied to working space 254 following each bolus. Working space 254 is then sorted, with identification of time interval groups and bolus time intervals done by program 250 using the bolus times stored in working space 254. As before, definitions of time interval groups and maximum bolus time interval duration from control data 259 are used by program 250 during the process of identification of time interval groups and bolus time intervals.

Medical infusion pumps other than the exemplary insulin pump described above may be programmed to produce boluses for reasons unrelated to meals, and the default maximum bolus interval duration would have to accommodate the needs of the particular application of that type of infusion pump.

FIG. 7 is similar to FIG. 5A, including the same bolus times in bolus time table 252. However, instead of having a separate time interval group for each day of the week, a single time interval group, time interval group 253h, covers weekdays; a second time interval group 253i covers Saturdays, and a third time interval group 253j covers Sundays. For those whose weekday meals (in the case of insulin medical infusion pumps, for example) are similar for each weekday, program 250 will have more bolus times in most or all bolus time intervals. For example, since a new "breakfast bolus time", e.g., value during a "breakfast bolus time interval" is added daily during the weekdays, instead of once per week as shown in FIG. 5A. Sorting of all the bolus times in time interval group 253h is performed as described earlier with respect to time interval group 253a to facilitate identification of bolus time intervals, as well as to simplify identification of when a current time equals a calculated alert time to activate alert mechanism 212.

Although sorting of bolus times within one or more time interval groups greatly simplifies identification of bolus time intervals and activation of alerts, and has been discussed in some detail, the present invention contemplates any process of identifying bolus time intervals and determination of times to activate alert mechanism 212.

Figure 8:
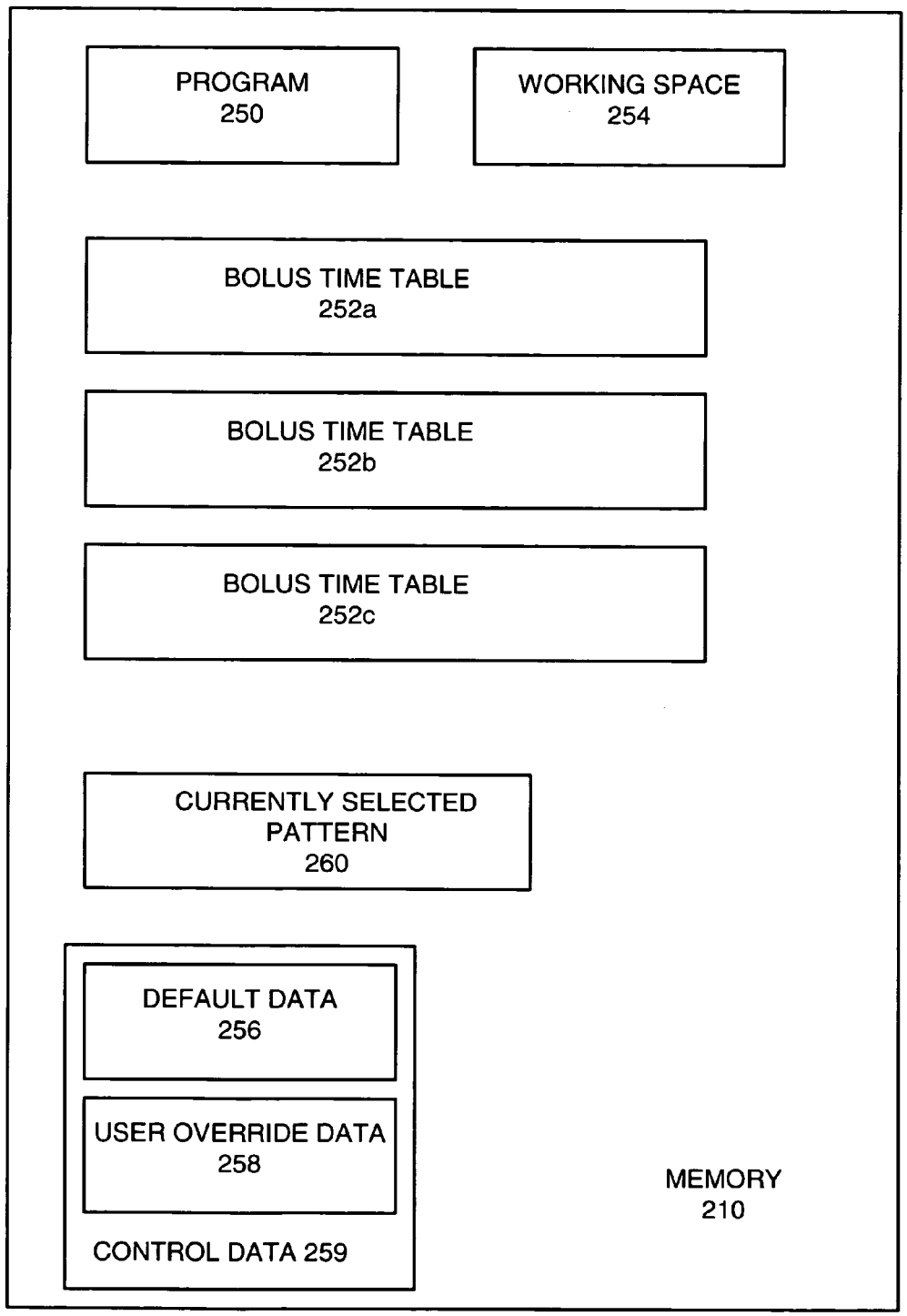
FIG. 8 is a block diagram showing contents of a memory of a medical infusion pump in which multiple bolus time tables are allocated, with a pointer controlling which bolus time table to use.

FIG. 8 is similar to FIG. 4, showing contents of memory 210. However, three bolus time tables, 252a, 252b, 252c are incorporated instead of single bolus time table 252. Some infusion pump users may have schedules that change, and bolus times that change with their schedules. Again using a diabetic as an example, the diabetic may have a job that involves shift work, working first shift for a first month, working second shift during a second month, and working third shift for a third month, repeating the work shift pattern in subsequent months. The diabetic's mealtimes, and therefore, the bolus patterns, will change monthly for such a work schedule. Three bolus time tables will suffice to accommodate that diabetic. Bolus time table 252a is selected by the user, by using keypad 104, a computer interface (not shown), or other suitable means, to cause currently selected pattern 260 to point to bolus time table 252a during the user's first shift work schedule. When moved to second shift, the user uses keypad 104, the computer interface, or other suitable means, to cause currently selected pattern 260 to point to bolus time table 252b. Similarly, when the user is shifted to third shift, the user uses keypad 104, a computer interface, or other suitable means, to cause currently selected pattern 260 to point to bolus time table 252c. Currently selected pattern 260 contains any value that can be used by program 250 to determine which bolus time table to use. For example, currently selected pattern 260 can be an address of a selected bolus time table, an index, or any other information that identifies to program 250 which bolus time table to use. Any number of bolus time tables is contemplated. Currently selected pattern 260 is advantageously stored in nonvolatile storage.

Figure 9:
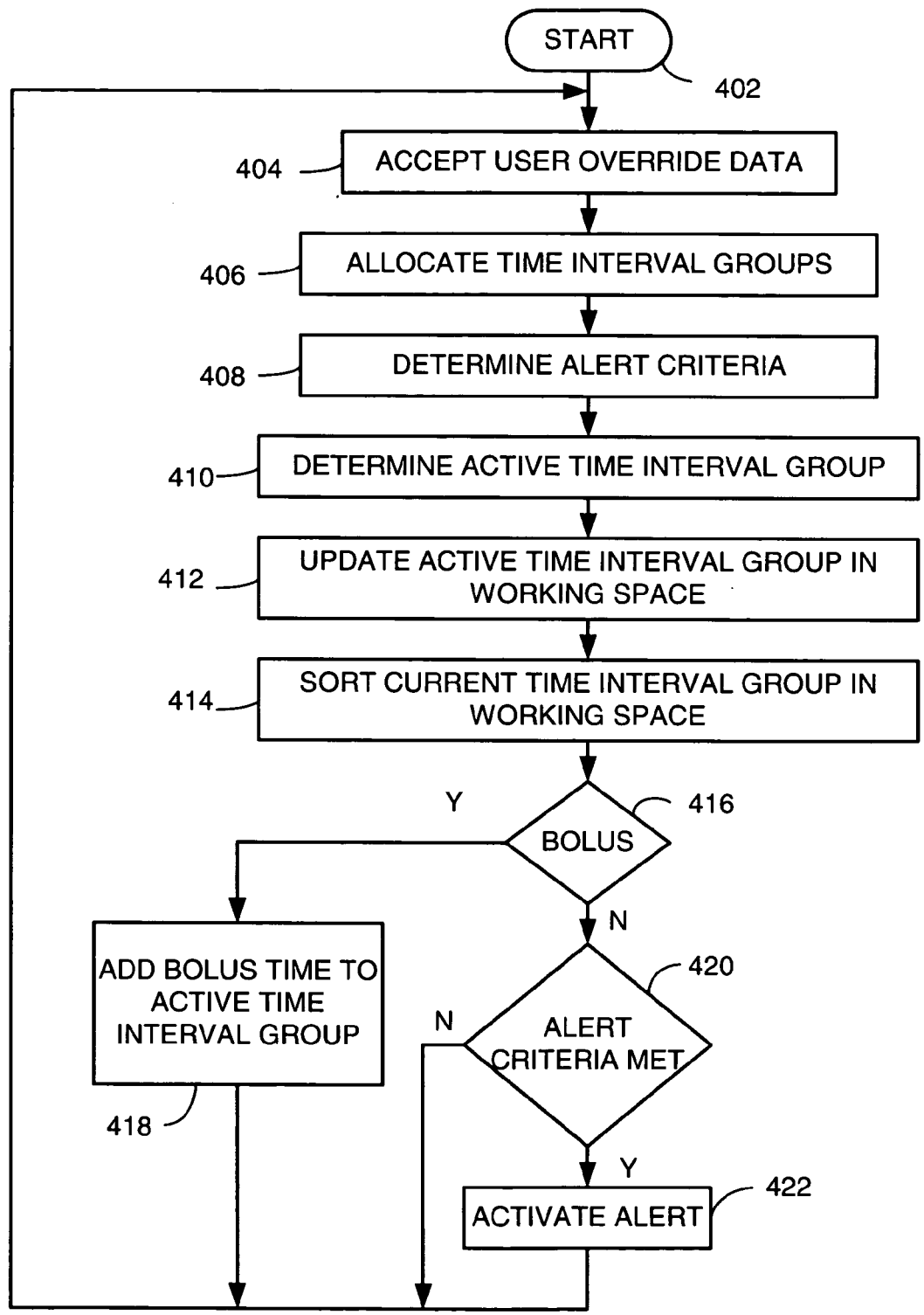
FIG. 9 is a flow chart of a method used in a medical infusion pump to "learn" when a user usually takes boluses in various time interval groups, and activate one or more alerts associated with bolus time intervals.

FIG. 9 shows a high level flow chart of a method of alerting a user of a medical infusion pump according to an embodiment of the present invention. The method is stored as executable instructions in program 250 (FIG. 4) of memory 210 (FIG. 4) and executed in processor 200 (FIG. 2).

The method begins at step 402. In step 404, any user overrides of default data are entered into the medical infusion pump, using a keypad on the medical infusion pump, or via a link between the medical infusion pump and a computer. Contents of default data (default data 256 of FIG. 4) was described earlier. Some or all of the default data has optional user override data that is used by program 250 instead of the default data. In an implementation that does not include default data, the user must input all information needed to define time interval groups, maximum bolus time interval duration, and other values discussed earlier.

In step 406, one or more time interval groups are defined and allocated in storage, using control data (the default data or its user override data counterpart). Time interval groups are periods of time (e.g., days, groups of days, or any other suitable time periods during which a user's bolus patterns are expected to be similar).

In step 408, one or more alert criteria are determined, that is, what event(s) are to trigger an alert to the user. An alert criteria is met if the current time equals a calculated alert time and a bolus has not yet been taken in an active bolus time interval. An active time interval group is a time interval group corresponding to the current time. For example, if a time interval group is defined for "Monday", and the current time (including day) is during a "Monday" time interval group, that time interval group is active. Similarly, a bolus time interval is active if the current time is equal to or greater than an earliest time in the bolus time interval and equal to or less than the latest time in the bolus time interval, and the bolus time interval is in the active time interval group. If a predetermined anticipatory period is implemented, the active bolus time interval begins at the earliest time in the bolus time minus the predetermined anticipatory period. If a predetermined wait period is implemented, the active bolus time interval ends at the latest time in the bolus time interval plus the predetermined wait period. A number of alert criteria were described earlier. One example of alert criteria is when a current time equals a calculated alert time being an earliest bolus time of an active bolus time interval. Thus if the current day is Monday, the current time is 6:30, and a time interval group includes Mondays, and a bolus time interval has an earliest bolus time of 6:30, that criteria is met. Alert criteria can similarly be defined to be met when the current time equals a calculated alert time equal to the average of bolus times in the active bolus time interval and no bolus has yet been taken in the active bolus time interval. Another alert criteria can be defined to be met when the current time equals a calculated alert time that coincides with the latest bolus time in the active bolus time interval and no bolus has yet been taken in the active bolus time interval. An alert criteria can include a calculated alert time equal to a predetermined wait time plus the last bolus time in a bolus time interval. For example, if the user has not taken a bolus during an active bolus time interval, including a predetermined wait time of ten minutes, the an alert criteria can be created to alert the user of that condition. The current invention contemplates any alert criteria suitable to alert the user associated with a bolus time interval.

In step 410, the active time interval group is determined, using current time from a timer coupled to a processor in the medical infusion pump (timer 205 in FIG. 2). Typically the timer keeps track of day of the week, and time of day. In some embodiments, month of year is included. A history of when boluses are taken is stored in a bolus time table. Some embodiments have more than one bolus time table (bolus time table 252a, 252b, 252c, shown in FIG. 8), and program 250 (FIG. 2) identifies the proper bolus time table using a currently selected pattern (currently selected pattern 260 shown in FIG. 8), then uses current time to determine the active time interval group within the selected bolus time table.

In step 412, an active time interval group is updated in a working space in storage coupled to the processor, using some or the entire proper bolus time table. Although the processor can be programmed to search through the active time interval group, determine a number of bolus times that make up a bolus time interval, and compare the current time against the identified bolus time interval, use of a working space greatly facilitates the processing.

In step 414, the active time interval group is sorted in the working space. Examples of this process were given in discussion of FIG. 6.

In step 416 a check is made to see if a bolus has been taken since the last time step 416 was performed. If so, the current time is added as a bolus time in the active time interval group. If the time interval groups are implemented as a logical (or physical) FIFO as described earlier, the oldest bolus time in the active time interval group is discarded if the FIFO is full. Advantageously, the FIFO is initialized with null values that are not considered as valid bolus times by program 250. As bolus times are added, null values are discarded until the FIFO is full. Step 418 passes control back to step 404, which again checks to see if the user wishes to input override data. Advantageously, step 404 is quickly bypassed unless the user has activated a key on a keypad or otherwise taken action (e.g., activated a computer interface) to indicate that the user wishes to enter user override data.

If step 416 determines that a bolus has not been delivered since the last time step 416 was performed, control passes to step 420, which checks to see if an alert criteria has been met. An alert criteria is met if the current time is equal to a calculated alert time and a bolus has not yet been taken in the active bolus time interval. If an alert criteria has been met, control passes to step 422. In an embodiment, additional information is passed from step 420 to step 422 to indicate the nature of the alert criteria.

Step 422 activates the alert mechanism (alert mechanism 212 in FIG. 2). In an embodiment where additional information was passed from step 420, step 422 produces different alerts. For example, in an embodiment, if the current time is equal to a calculated alert time that is the earliest time in an active bolus time interval, a soft single beep is issued by the alert mechanism. If the current time is equal to a calculated alert time that is the T50 time (FIG. 3C) and a bolus has not yet been taken in the bolus time interval, two soft beeps are issued by the alert mechanism. If the current time is equal to a calculated alert time that is the T100 time (FIG. 3C) of the active bolus time period and a bolus has not yet been taken in the bolus time interval, three loud beeps are issued by the alert mechanism. Any variation of beeps (or vibrations or other means of alerting the user) responsive to different alert criteria being met are within the spirit and scope of the present invention.

The program that contains the steps described above, which are executable on a suitable processor, can be stored on and distributed as computer readable media as a program product. Examples of such computer readable media include, but are not limited to, magnetic tape, magnetic disks, DVD disks, CD ROMS, or computer networks, which include wide area networks (WANs), local area networks (LANs), and the internet.

What is claimed is:

1. A medical infusion pump, comprising:
an infusion pump processor in the medical infusion pump;
an actuator in the medical infusion pump coupled to the infusion pump processor suitable for delivering medicament doses to a user;
a storage coupled to the infusion pump processor, the storage further comprising more than one time interval groups, each of the more than one time interval groups being capable of storing one or more bolus time intervals;
an input device coupled to the infusion pump processor suitable to allow the user to cause a bolus to be delivered;
an alert mechanism coupled to the infusion pump processor suitable to warn the user; and
a timer coupled to the infusion pump processor capable of maintaining time information;
wherein the processor determines, using the user's history of boluses delivered by the medical infusion pump in each of the more than one time interval groups, the one or more bolus time intervals during which a bolus is usually taken by the user in the each of the more than one time interval groups, and, activating the alerting mechanism at one or more calculated alert times associated with an active bolus time interval in the one or more bolus time intervals, if a bolus has not been taken yet in the active bolus time interval.

2. The medical infusion pump of claim 1, wherein the user can define at least one of the more than one time interval groups.

3. A medical infusion pump, comprising:
an infusion pump processor in the medical infusion pump;
an actuator in the medical infusion pump coupled to the infusion pump processor suitable for delivering medicament doses;
a storage coupled to the infusion pump processor;
an input device coupled to the infusion pump processor suitable to allow a user to cause a bolus to be delivered;
an alert mechanism suitable to warn the user; and
a timer coupled to the infusion pump processor capable of maintaining time information;
wherein the processor determines, using the user's history of bolus deliveries by the pump, one or more bolus time intervals during which a bolus is usually taken by the user, and, activating the alerting mechanism at one or more calculated alert times associated with the one or more bolus time intervals.

4. The medical infusion pump of claim 3, wherein the alerting mechanism is activated when a current time equals a particular calculated alert time in the one or more calculated alert times of an active bolus time interval in the one or more of the bolus time intervals, and a bolus has not yet been taken during the active bolus time interval prior to the particular calculated alert time.

5. The medical infusion pump of claim 3, the storage including a bolus time table.

6. The medical infusion pump of claim 5, the bolus time table constructed as a FIFO (first in first out) structure.

7. The medical infusion pump of claim 5, the bolus time table constructed as a linearly addressable storage array.

8. The medical infusion pump of claim 5, the bolus time table partitioned into one or more time interval groups.

9. The medical infusion pump of claim 8, the bolus time table logically partitioned into one or more time interval groups.

10. The medical infusion pump of claim 9, wherein the bolus time table logical partitioning is determined by time table logical partition information in a control data.

11. The medical infusion pump of claim 10, wherein the control data includes time table logical partition information in a default data that can be overridden by user override logical partition information, if entered by the user.

12. The medical infusion pump of claim 8, the bolus time table physically partitioned into one or more time interval groups.

13. The medical infusion pump of claim 8, further comprising a working space in storage large enough to store a largest time interval group of the one or more time interval groups.

14. The medical infusion pump of claim 3, comprising:
a plurality of bolus time tables in the storage;
means for allowing the user to specify to the infusion pump processor a particular bolus time table in the plurality of bolus time tables to use.

15. A method of alerting a user of a medical infusion pump, comprising the steps of:
storing, in the medical infusion pump, time information at which boluses are taken by the user;
determining, by the medical infusion pump, one or more bolus time intervals during which a bolus is usually taken by the user, using the time information; and
alerting the user when a current time equals one or more calculated alert times associated with an active bolus time interval until a bolus is taken during the active bolus time interval.

16. The method of claim 15, further comprising the step of logically partitioning a storage in the infusion pump into one or more time interval groups, a time interval group corresponding to a recurring period of time during which the user's bolus pattern does not substantially vary.

17. The method of claim 16, the step of logically partitioning a storage in the infusion pump into one or more time interval groups is at least partially determined by the user.

18. The method of claim 16, the step of logically partitioning the storage comprises the step of creating a separate time interval group for each day of a week.

19. The method of claim 16, the step of logically partitioning the storage comprises the step of creating a first time interval group that includes Mondays, Tuesdays, Wednesdays, Thursdays, and Fridays.

20. The method of claim 19, the step of logically partition the storage further comprising the step of creating a second time interval group that includes Saturdays.

21. The method of claim 19, the step of logically partitioning the storage further comprising the step of creating a third time interval group that includes Sundays.

22. The method of claim 15, the step of determining, by the medical infusion pump, one or more bolus time intervals, further includes sorting the time information at which boluses are taken by the user.

23. The method of claim 15, the step of determining, by the medical infusion pump, one or more bolus time intervals, further comprising use of a maximum bolus time interval duration to distinguish a first bolus time interval from a second time interval.

24. The method of claim 15, the step of alerting the user when a current time equals one or more calculated alert times during an active bolus time interval until a bolus is taken during the active bolus time interval further comprises the step of testing one or more alert criteria, and, if the one or more alert criteria is satisfied, activating an alert mechanism.

25. The method of claim 24, wherein the one or more alert criteria includes a current time equaling a first particular calculated alert time that is a predetermined anticipatory period prior to the first bolus time of the active bolus time interval.

26. The method of claim 24, wherein the one or more alert criteria includes a current time equaling a second particular calculated alert time that is an earliest bolus time of the active bolus time interval.

27. The method of claim 24, wherein the one or more alert criteria includes a current time equaling a third particular calculated alert time during the active bolus time interval, the third particular calculated alert time being an average of all bolus times in the active bolus time interval.

28. The method of claim 24, wherein the one or more alert criteria includes a current time equal to a fourth particular calculated alert time that is later than the latest bolus time of the active bolus time interval.

29. The method of claim 24, wherein the step of alerting the user further includes activating the alert mechanism differently responsive to which of the alert criteria is satisfied.

30. A program product, distributed on computer-readable media that, when executed on a suitable processor, executes the steps of claim 15.

31. A method of alerting a user of a medical infusion pump, comprising the steps of:
learning, by the medical infusion pump, one or more bolus time intervals during which a user of the medical infusion pump normally takes a bolus; and
alerting the user at one or more calculated alert times associated with an active bolus time interval in the one or more bolus time intervals if a bolus has not yet been taken prior to the calculated alert time.

32. The method of claim 31, further comprising the step of alerting the user at a first particular calculated alert time that is a predetermined anticipatory period prior to a first bolus time of the particular bolus time period.

33. The method of claim 31, further comprising the step of alerting the user at a second particular calculated alert time that is a the earliest bolus time in the active bolus time period.

34. The method of claim 31, further comprising the step of alerting the user at a third particular calculated alert time during the active bolus time interval.

35. The method of claim 31, further comprising the step of alerting the user at a fourth particular calculated alert time that is later than the latest bolus time in the active bolus time interval.

36. A program product, distributed on computer-readable media that, when executed on a suitable processor, executes the steps of claim 31.

37. A medical infusion pump, comprising:
a timer; and
an alerting mechanism;
wherein the medical infusion pump determines, using a user's history of bolus deliveries by the medical infusion pump, one or more bolus time intervals during which a bolus is usually taken by the user, and, activating the alerting mechanism at one or more calculated alert times associated with the one or more bolus time intervals.

38. The medical infusion pump of claim 37, wherein the medical infusion pump has more than one time interval groups, each time interval group containing one or more of the bolus time intervals.

39. The medical infusion pump of claim 37, wherein the medical infusion pump is an insulin pump.

* * * * *